(12) United States Patent
Kadowaki et al.

(10) Patent No.: US 7,419,955 B2
(45) Date of Patent: Sep. 2, 2008

(54) METHOD FOR TREATING ARTERIOSCLEROSIS

(75) Inventors: Takashi Kadowaki, Tokyo (JP); Toshimasa Yamauchi, Tokyo (JP); Naoto Kubota, Tokyo (JP); Yasuo Terauchi, Tokyo (JP); Tetsuya Kubota, Tokyo (JP); Tetsuo Noda, Tokyo (JP); Ryozo Nagai, Tokyo (JP); Yasushi Imai, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 349 days.

(21) Appl. No.: 10/514,715

(22) PCT Filed: May 26, 2003

(86) PCT No.: PCT/JP03/06518

§ 371 (c)(1),
(2), (4) Date: Nov. 23, 2004

(87) PCT Pub. No.: WO03/099319

PCT Pub. Date: Dec. 4, 2003

(65) Prior Publication Data

US 2006/0166873 A1    Jul. 27, 2006

(30) Foreign Application Priority Data

May 24, 2002    (JP)    .............................. 2002-151220

(51) Int. Cl.
*A61K 38/00*    (2006.01)
(52) U.S. Cl. ....................................................... 514/12
(58) Field of Classification Search ...................... None
See application file for complete search history.

(56) References Cited

U.S. PATENT DOCUMENTS 6,344,441 B1 * 2/2002 Bihain et al. .................. 514/12

FOREIGN PATENT DOCUMENTS

| EP | 1033134 A1 | * | 9/2000 |
| WO | WO 99/07736 | * | 2/1999 |
| WO | 02/061076 | | 8/2002 |

OTHER PUBLICATIONS

Arteriosclerosis/atherosclerosis (MayoClinic.com).*
Ouchi, Noriyuki et al., Adipocyte-dervied plasma portel, adiponectin, suppesses lipid accumulation and class A scavenger receptor expression in human monocyte-derived macrohages, Circulation, vol. 103, No. 8, pp. 1057 to 1063, 2001.
Ouchi, Noriyuki et al., A novel adipocyte-derived plasma protein, adiponectin, suppresses scavenger receptor expression in human monocyte-derived macrophages., Circulation, vol. 110, No. 18, Suppl., pp. I.751. Meeting Info. : 72nd Scientific Sessions of the America Heart Association, 1999.
Kihara, Shinji et al., Anti-atherogenic property of adipocyte-derived plasma protein adiponectin., Journal of Molecular and Cellular Cardiology, vol. 32, No., pp. A93, 2000.
Maeda, Kazuhisa et al., cDNA cloning and expression of a novel adipose specific collagen-like fector, apM1 (adipose most abundant gene transcript 1), Biochemical and Biophysical Research Communications, vol. 221, No. 2, pp. 286 to 289, 1996.
Okamoto, Yoshihisa et al., Adiponectin Reduces Atherosclerosis in Apolipoprotein E-Deficient Mice, Circulation, vol. 106, No. 22, pp. 2767-2770, Nov. 26, 2002.
U.S. Appl. No. 10/514,716, filed Nov. 23, 2004, Kadowaki et al.
U.S. Appl. No. 10/514,715, filed Nov. 23, 2004, Kadowaki et al.
U.S. Appl. No. 10/502,051, filed Jul. 30, 2004, Kadowaki et al.
Tsu-Shuen Tsao, et al., "ACRP30, a new hormone controlling fat and glucose metabolism", European Journal of Pharmacology, XP 002319451, vol. 440, No. 2-3, Apr. 12, 2002, pp. 213-221.
Anders H. Berg, et al., "ACRP30/ adiponectin: an adipokine regulating glucose and lipid metabolism", Trends in Endocrinology & Metabolism, XP 002286670, vol. 13, No. 2, Mar. 2002, pp. 84-89.
Joachim Fruebis, et al., "Proteolytic cleavage product of 30-kDa adipocyte complement-related protein increases fatty acid oxidation in muscle and causes weight loss in mice", Proceedings of the National Academy of Sciences, XP 002242791, vol. 98, No. 4, Feb. 13, 2001, pp. 2005-2010.

* cited by examiner

*Primary Examiner*—Robert Landsman
*Assistant Examiner*—Gyan Chandra
(74) *Attorney, Agent, or Firm*—Oblon, Spivak, McClelland, Maier & Neustadt, P.C.

(57) ABSTRACT

A scavenger receptor A expression down-regulator and a drug for preventing or treating arteriosclerosis which contain, as the active ingredient, a C-terminal globular domain of adiponectin, adiponectin, or a gene encoding the domain or adiponectin. According to the present invention, there is provided a preventive or therapeutic agent capable of directly preventing intimal thickening, which constitutes an essential feature of arteriosclerosis. This effect can be attained through arresting the onset and development of arteriosclerosis by reducing the expression level of scavenger receptor A in arterial walls and preventing lipid buildup in macrophages.

3 Claims, 14 Drawing Sheets

(1)

(2)

a    apoE-/- b    gAdTg apoE-/-

SEQUENCE LISTING

<160> NUMBER OF SEQ ID NOS: 4

<210> SEQ ID NO 1
<211> LENGTH: 735
<212> TYPE: DNA

<213> ORGANISM: Homo sapiens
<220> FEATURE:
<221> NAME/KEY: CDS
<222> LOCATION: (1)..(735)

<400> SEQUENCE: 1

| | | | | | | | | | | | | | | | | |
|---|---|---|---|---|---|---|---|---|---|---|---|---|---|---|---|---|
| atg | ctg | ttg | ctg | gga | gct | gtt | cta | ctg | cta | tta | gct | ctg | ccc | ggt | cat | 48 |
| Met | Leu | Leu | Leu | Gly | Ala | Val | Leu | Leu | Leu | Leu | Ala | Leu | Pro | Gly | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | cag | gaa | acc | acg | act | caa | ggg | ccc | gga | gtc | ctg | ctt | ccc | ctg | ccc | 96 |
| Asp | Gln | Glu | Thr | Thr | Thr | Gln | Gly | Pro | Gly | Val | Leu | Leu | Pro | Leu | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | ggg | gcc | tgc | aca | ggt | tgg | atg | gcg | ggc | atc | cca | ggg | cat | ccg | ggc | 144 |
| Lys | Gly | Ala | Cys | Thr | Gly | Trp | Met | Ala | Gly | Ile | Pro | Gly | His | Pro | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| cat | aat | ggg | gcc | cca | ggc | cgt | gat | ggc | aga | gat | ggc | acc | cct | ggt | gag | 192 |
| His | Asn | Gly | Ala | Pro | Gly | Arg | Asp | Gly | Arg | Asp | Gly | Thr | Pro | Gly | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggt | gag | aaa | gga | gat | cca | ggt | ctt | att | ggt | cct | aag | gga | gac | atc | 240 |
| Lys | Gly | Glu | Lys | Gly | Asp | Pro | Gly | Leu | Ile | Gly | Pro | Lys | Gly | Asp | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggt | gaa | acc | gga | gta | ccc | ggg | gct | gaa | ggt | ccc | cga | ggc | ttt | ccg | gga | 288 |
| Gly | Glu | Thr | Gly | Val | Pro | Gly | Ala | Glu | Gly | Pro | Arg | Gly | Phe | Pro | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | caa | ggc | agg | aaa | gga | gaa | cct | gga | gaa | ggt | gcc | tat | gta | tac | cgc | 336 |
| Ile | Gln | Gly | Arg | Lys | Gly | Glu | Pro | Gly | Glu | Gly | Ala | Tyr | Val | Tyr | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | gca | ttc | agt | gtg | gga | ttg | gag | act | tac | gtt | act | atc | ccc | aac | atg | 384 |
| Ser | Ala | Phe | Ser | Val | Gly | Leu | Glu | Thr | Tyr | Val | Thr | Ile | Pro | Asn | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | att | cgc | ttt | acc | aag | atc | ttc | tac | aat | cag | caa | aac | cac | tat | gat | 432 |
| Pro | Ile | Arg | Phe | Thr | Lys | Ile | Phe | Tyr | Asn | Gln | Gln | Asn | His | Tyr | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | tcc | act | ggt | aaa | ttc | cac | tgc | aac | att | cct | ggg | ctg | tac | tac | ttt | 480 |
| Gly | Ser | Thr | Gly | Lys | Phe | His | Cys | Asn | Ile | Pro | Gly | Leu | Tyr | Tyr | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gcc | tac | cac | atc | aca | gtc | tat | atg | aag | gat | gtg | aag | gtc | agc | ctc | ttc | 528 |
| Ala | Tyr | His | Ile | Thr | Val | Tyr | Met | Lys | Asp | Val | Lys | Val | Ser | Leu | Phe | |
| | | | 165 | | | | | 170 | | | | | 175 | | | |

| | | | | | | | | | | | | | | | | |
|---|---|---|---|---|---|---|---|---|---|---|---|---|---|---|---|---|
| aag | aag | gac | aag | gct | atg | ctc | ttc | acc | tat | gat | cag | tac | cag | gaa | aat | 576 |
| Lys | Lys | Asp | Lys | Ala | Met | Leu | Phe | Thr | Tyr | Asp | Gln | Tyr | Gln | Glu | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| aat | gtg | gac | cag | gcc | tcc | ggc | tct | gtg | ctc | ctg | cat | ctg | gag | gtg | ggc | 624 |
| Asn | Val | Asp | Gln | Ala | Ser | Gly | Ser | Val | Leu | Leu | His | Leu | Glu | Val | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | caa | gtc | tgg | ctc | cag | gtg | tat | ggg | gaa | gga | gag | cgt | aat | gga | ctc | 672 |
| Asp | Gln | Val | Trp | Leu | Gln | Val | Tyr | Gly | Glu | Gly | Glu | Arg | Asn | Gly | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | gct | gat | aat | gac | aat | gac | tcc | acc | ttc | aca | ggc | ttt | ctt | ctc | tac | 720 |
| Tyr | Ala | Asp | Asn | Asp | Asn | Asp | Ser | Thr | Phe | Thr | Gly | Phe | Leu | Leu | Tyr | |
| 225 | | | | | 230 | | | | | 235 | | | | | 240 | |

| | | | | | |
|---|---|---|---|---|---|
| cat | gac | acc | aac | tga | 735 |
| His | Asp | Thr | Asn | | |

<210> SEQ ID NO 2
<211> LENGTH: 244
<212> TYPE: PRT
<213> ORGANISM: Homo sapiens

<400> SEQUENCE: 2

-continued

```
Met Leu Leu Leu Gly Ala Val Leu Leu Leu Ala Leu Pro Gly His
1               5                   10                  15

Asp Gln Glu Thr Thr Thr Gln Gly Pro Gly Val Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 3
<211> LENGTH: 1276
<212> TYPE: DNA
<213> ORGANISM: Mus musculus
<220> FEATURE:
<221> NAME/KEY: CDS
<222> LOCATION: (46)..(789)

<400> SEQUENCE: 3
ctctaaagat tgtcagtgga tctgacgaca ccaaaagggc tcagg atg cta ctg ttg      57
                                                Met Leu Leu Leu
                                                1 caa gct ctc ctg ttc ctc tta atc ctg ccc agt cat gcc gaa gat gac      105
Gln Ala Leu Leu Phe Leu Leu Ile Leu Pro Ser His Ala Glu Asp Asp
5               10                  15                  20 gtt act aca act gaa gag cta gct cct gct ttg gtc cct cca ccc aag      153
Val Thr Thr Thr Glu Glu Leu Ala Pro Ala Leu Val Pro Pro Pro Lys
            25                  30                  35 gga act tgt gca ggt tgg atg gca ggc atc cca gga cat cct ggc cac      201
Gly Thr Cys Ala Gly Trp Met Ala Gly Ile Pro Gly His Pro Gly His
        40                  45                  50 aat ggc aca cca ggc cgt gat ggc aga gat ggc act cct gga gag aag      249
Asn Gly Thr Pro Gly Arg Asp Gly Arg Asp Gly Thr Pro Gly Glu Lys
    55                  60                  65 gga gag aaa gga gat gca ggt ctt ctt ggt cct aag ggt gag aca gga      297
```

```
                                                                                        -continued Gly Glu Lys Gly Asp Ala Gly Leu Leu Gly Pro Lys Gly Glu Thr Gly
         70                  75                  80 gat gtt gga atg aca gga gct gaa ggg cca cgg ggc ttc ccc gga acc       345
Asp Val Gly Met Thr Gly Ala Glu Gly Pro Arg Gly Phe Pro Gly Thr
 85                  90                  95                 100 cct ggc agg aaa gga gag cct gga gaa gcc gct tat atg tat cgc tca       393
Pro Gly Arg Lys Gly Glu Pro Gly Glu Ala Ala Tyr Met Tyr Arg Ser
                105                 110                 115 gcg ttc agt gtg ggg ctg gag acc cgc gtc act gtt ccc aat gta ccc       441
Ala Phe Ser Val Gly Leu Glu Thr Arg Val Thr Val Pro Asn Val Pro
            120                 125                 130 att cgc ttt act aag atc ttc tac aac caa cag aat cat tat gac ggc       489
Ile Arg Phe Thr Lys Ile Phe Tyr Asn Gln Gln Asn His Tyr Asp Gly
        135                 140                 145 agc act ggc aag ttc tac tgc aac att ccg gga ctc tac tac ttc tct       537
Ser Thr Gly Lys Phe Tyr Cys Asn Ile Pro Gly Leu Tyr Tyr Phe Ser
    150                 155                 160 tac cac atc acg gtg tac atg aaa gat gtg aag gtg agc ctc ttc aag       585
Tyr His Ile Thr Val Tyr Met Lys Asp Val Lys Val Ser Leu Phe Lys
165                 170                 175                 180 aag gac aag gcc gtt ctc ttc acc tac gac cag tat cag gaa aag aat       633
Lys Asp Lys Ala Val Leu Phe Thr Tyr Asp Gln Tyr Gln Glu Lys Asn
                185                 190                 195 gtg gac cag gcc tct ggc tct gtg ctc ctc cat ctg gag gtg gga gac       681
Val Asp Gln Ala Ser Gly Ser Val Leu Leu His Leu Glu Val Gly Asp
            200                 205                 210 caa gtc tgg ctc cag gtg tat ggg gat ggg gac cac aat gga ctc tat       729
Gln Val Trp Leu Gln Val Tyr Gly Asp Gly Asp His Asn Gly Leu Tyr
        215                 220                 225 gca gat aac gtc aac gac tct aca ttt act ggc ttt ctt ctc tac cat       777
Ala Asp Asn Val Asn Asp Ser Thr Phe Thr Gly Phe Leu Leu Tyr His
    230                 235                 240 gat acc aac tga ctgcaactac ccatagccca tacaccagga gaatcatgga          829
Asp Thr Asn
245 acagtcgaca cactttcagc ttagtttgag agattgattt tattgcttag tttgagagtc     889 ctgagtatta tccacacgtg tactcacttg ttcattaaac gactttataa aaataatttt     949 gtgttcctag tccagaaaaa aaggcactcc ctggtctcca cgactcttac atggtagcaa    1009 taacagaatg aaaatcacat ttggtatggg ggcttcacaa tattcgcatg actgtctgga    1069 agtagaccat gctatttttc tgctcactgt acacaaatat tgttcacata acccctataa    1129 tgtaaatatg aaatacagtg attactcttc tcacaggctg agtgtatgaa tgtctaaaga    1189 cccataagta ttaaagtggt agggataaat tggaaaaaaa aaaaaaaaaa aagaaaaact    1249 ttagagcaca ctggcggccg ttactag                                         1276

<210> SEQ ID NO 4
<211> LENGTH: 247
<212> TYPE: PRT
<213> ORGANISM: Mus musculus

<400> SEQUENCE: 4

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45
```

-continued

```
His Pro Gly His Asn Gly Thr Pro Gly Arg Asp Gly Arg Asp Gly Thr
        50                  55                  60

Pro Gly Glu Lys Gly Glu Lys Gly Asp Ala Gly Leu Leu Gly Pro Lys
65                      70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245
```

METHOD FOR TREATING ARTERIOSCLEROSIS

TECHNICAL FIELD

The present invention relates to a drug for preventing or treating arteriosclerosis.

BACKGROUND ART

The term "arteriosclerosis" refers to a pathological condition where the walls of an artery lose elasticity and become brittle. Arteriosclerosis is one of key factors causing aduet diseases, including cerebral hemorrhage, cerebral infarction, myocardial infarction, and nephrosclerosis. Known causes of arteriosclerosis include hyperlipidemia, and bacteria, viruses, or lipid peroxide in blood. However, the pathogenesis of arteriosclerosis has not yet been fully elucidated. In any case, since arteriosclerosis has been observed to begin with thickening of arterial walls caused by damage to the arterial intima or endothelium, there is keen demand for development of a drug capable of inhibiting thickening of the arterial intima.

Accordingly, an object of the present invention is to provide a drug which is effective for preventing or treating arteriosclerosis.

DISCLOSURE OF THE INVENTION

Under the above circumstance, the present inventors have devoted their research efforts to pharmacological actions of adiponectin, which is known to have an insulin resistance reducing effect, and have found that adiponectin-gene-deficient mice show significantly thickened arterial intima; and that adiponectin, a C-terminal globular domain thereof, or a gene thereof is useful as a preventive or therapeutic drug for arteriosclerosis, on the basis of their experimental results that when apoE-deficient mice, which are employed as atherosclerosis onset model mice, are manipulated to over-express adiponectin, in particular, the C-terminal globular domain of adiponectin, the onset of arteriosclerosis is suppressed. In addition, since over-expression of adiponectin lowers the expression level of scavenger receptor A without significantly affecting the levels of free fatty acid, neutral fat, or total cholesterol in blood, the inventors have concluded that the arteriosclerosis preventive action of adiponectin lowers the expression level of scavenger receptor A, whereby accumulation of lipids in macrophages is prevented. The present invention has been accomplished on the basis of these findings.

Accordingly, the present invention provides a drug for preventing or treating arteriosclerosis, the drug containing, as an active ingredient thereof, a C-terminal globular domain of adiponectin, adiponectin, or a gene encoding the C-terminal globular domain of adiponectin or the adiponectin.

The present invention also provides a scavenger receptor A expression down-regulator which contains, as an active ingredient thereof, a C-terminal globular domain of adiponectin, adiponectin, or a gene encoding the C-terminal globular domain of adiponectin or the adiponectin.

The present invention also provides use, in the manufacture of a drug for preventing or treating arteriosclerosis, of a C-terminal globular domain of adiponectin, adiponectin, or a gene encoding the C-terminal globular domain of adiponectin or the adiponectin.

The present invention also provides use, in the manufacture of a scavenger receptor A expression down-regulator, of a C-terminal globular domain of adiponectin, adiponectin, or a gene encoding the C-terminal globular domain of adiponectin or the adiponectin.

The present invention also provides a method for treating arteriosclerosis, comprising administering, to a subject in need thereof, an effective amount of a C-terminal globular domain of adiponectin, adiponectin, or a gene encoding the C-terminal globular domain of adiponectin or the adiponectin.

The present invention also provides a method for down-regulating the expression level of scavenger receptor A in a patient, comprising administering to the patient an effective amount of a C-terminal globular domain of adiponectin, adiponectin, or a gene encoding the C-terminal globular domain of adiponectin or the adiponectin.

BEST MODE FOR CARRYING OUT THE INVENTION

Figure 1:
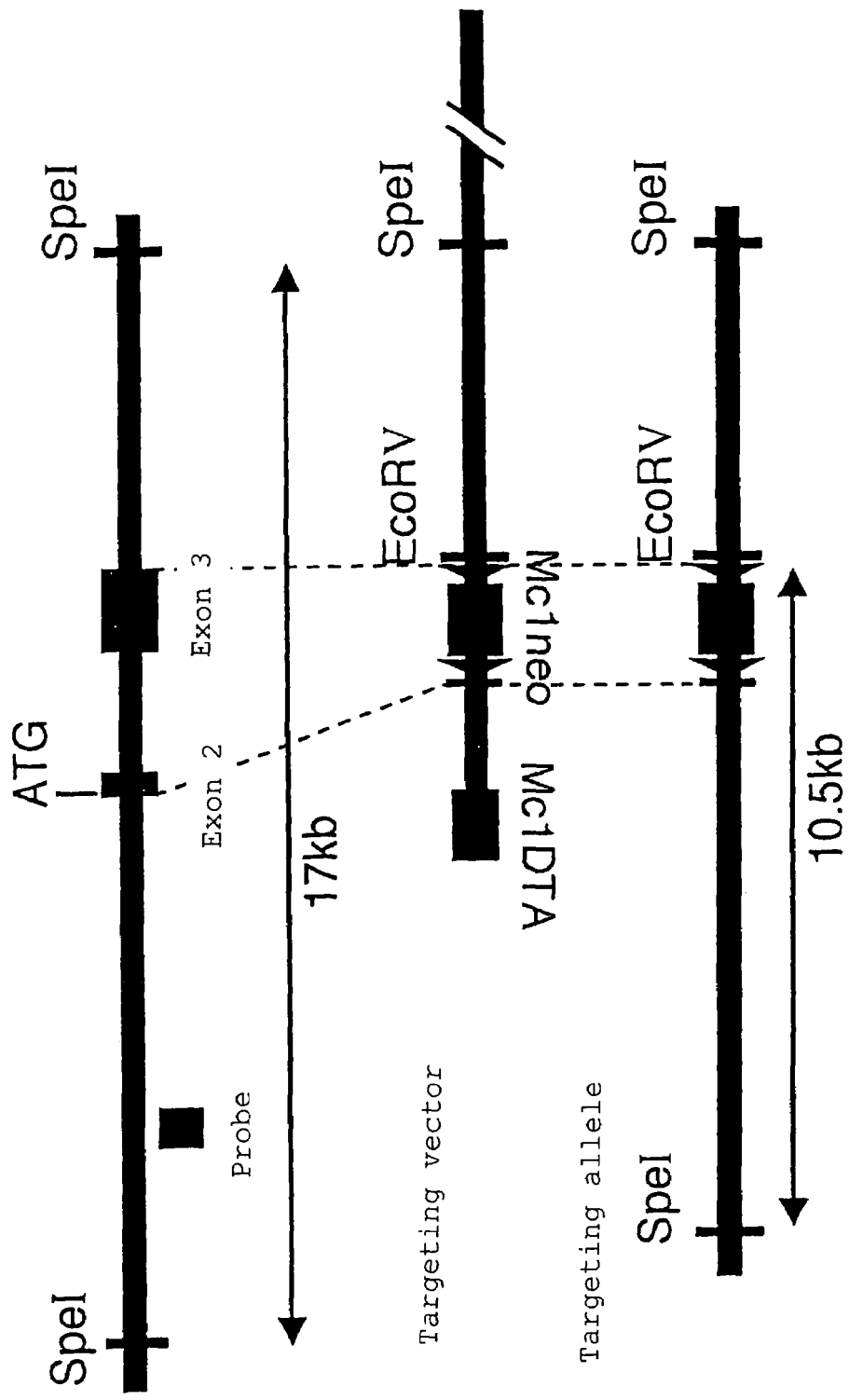
FIG. 1 schematically shows a gene targeting performed on adiponectin gene deficiency, in which, a restriction map of a mouse adiponectin gene (top), an adiponectin gene targeting vector (middle), and a deduced targeting allele (bottom).

Adiponectin, which is employed in the present invention, has already been cloned (Maeda, K. et al., Biochem. Biophys. Res. Commun. 221, 286-296 (1996), Nakano, Y. et al., J. Biochem. (Tokyo) 120, 802-812 (1996)), and is available through known means. SEQ ID NOs: 1 and 2 show the nucleotide sequence and the amino acid sequence of human adiponectin. Adiponectin is composed of an N-terminal collagen-like sequence (cAd) a C-terminal globular domain (gAd; in SEQ ID NO: 1, amino acid Nos. 114 to 239 or 111 to 242). The C-terminal globular domain (gAd) is preferred as it provides stronger arteriosclerosis preventive and therapeutic effects than full length adiponectin. SEQ ID NOs: 3 and 4 show the nucleotide sequence and the amino acid sequence of mouse adiponectin. The N-terminal collagen-like sequence (cAd) of the mouse adiponectin stretches from 45 to 109 (amino acid No.), and the C-terminal globular domain (gAd) stretches from 110 to 247 (amino acid No.). According to the present invention, not only proteins comprising the amino acid sequence of any of SEQ ID NOs: 1 to 4 or an amino acid sequence having the gAd domain, but also a protein comprising a modified amino acid sequence derived from substitution, deletion, or addition of one or more amino acid residues of any of these amino acid sequences may be employed, so long as it provides an effect as exhibited by adiponectin. Examples of such mutated proteins include those having 80% or higher homology, preferably 90% or higher homology, to any of the amino acid sequences of SEQ ID NOs: 1 to 4 or an amino acid sequence including the gAd domain.

Examples of the gene which is employed in the present invention include the genes coding for adiponectin (i.e., SEQ ID NOs: 1 and 3) and a gene coding for gAd. Also, there may be employed a gene having a nucleotide sequence capable of hybridizing with any of these genes under stringent conditions.

Adiponectin or a polypeptide which forms a portion of adiponectin (including gAd) may be isolated from cells containing the same. However, since a gene coding for adiponectin has already been cloned, the adiponectin or the polypeptide may be prepared through a DNA recombinant technique; i.e., making use of transformant cells created by use of expression vectors produced through use of the gene.

As will be described hereinbelow, adiponectin-deficient mice exhibit high levels of neutral fat in blood, but their cholesterol levels are comparable to those of wild-type mice. Moreover, adiponectin-deficient mice, representing an arteriosclerosis model, exhibited intima thickening which was twice the thickness as observed in wild-type mice. In contrast, when apoE-deficient mice, which represent a spontaneous atherosclerosis model, are caused to over-express gAd, they exhibit a significant reduction in arteriosclerotic area, preventing development of arteriosclerosis. However, overexpression of gAd induced in apoE-deficient mice only insignificantly affect general risk factors for arteriosclerosis, such as body weight and blood sugar, and free fatty acid, neutral fat, and total cholesterol in blood. On the other hand, overexpression of gAd induced in apoE-deficient mice was found to exhibit a lowered expression of scavenger receptor A in arterial walls. Scavenger receptor A is a receptor which, when macrophages engulf modified LDL, binds to the modified LDL on the surface of a cell, and is known to play a key role as a receptor which triggers the onset of arteriosclerosis.

Accordingly, adiponectin, gAd, or a gene coding for adiponectin or gAd is useful as a down-regulator of scavenger receptor A expression, or as a drug for preventing or treating arteriosclerosis. In particular, gAd or a gene encoding gAd is very useful in that it exhibits a more potent down-regulating effect on expression of a scavenger receptor as compared with adiponectin, and stronger preventive or therapeutic effect.

For administering the drug of the present invention to a mammal including a human, pharmaceutical compositions of a variety of dosage forms may be produced through incorporation of a pharmacologically acceptable carrier to any of the aforementioned active ingredients. Among such dosage forms, preparations for injection are preferred. Examples of the pharmacologically acceptable carrier include distilled water, a solubilizer, a stabilizer, an emulsifier, and a buffer. The dose of any of the drugs may differ depending on the condition of the disease, sex, body weight, etc., and may range from 0.1 μg to 10 mg/day or thereabouts, as reduced to the amount of adiponectin or gAd.

EXAMPLES

The present invention will next be described in more detail by way of examples, which should not construed as limiting the invention thereto.

A. Methods (1) Preparation of Knockout Mice

Screening of a 129/Sv mouse genomic library was performed using adiponectin cDNA as a probe, whereby a plurality of clones harboring a gene encoding adiponectin were obtained. A targeting vector was constructed, in which the region stretching from the translation initiation site to the translation termination site had been replaced by a neomycin-resistant gene. ES cells were transfected with the resultant targeting vector. Screening was performed through Southern blotting, whereby homologous recombinants of 5 clones were confirmed. Chimeric mice were created by means of microinjection, and the mice were crossbred with Bl/6 to thereby produce F1, and then F2.

Briefly, an adiponectin-gene-deficient mouse was produced through homologous recombination as shown in FIG.

Figure 2:
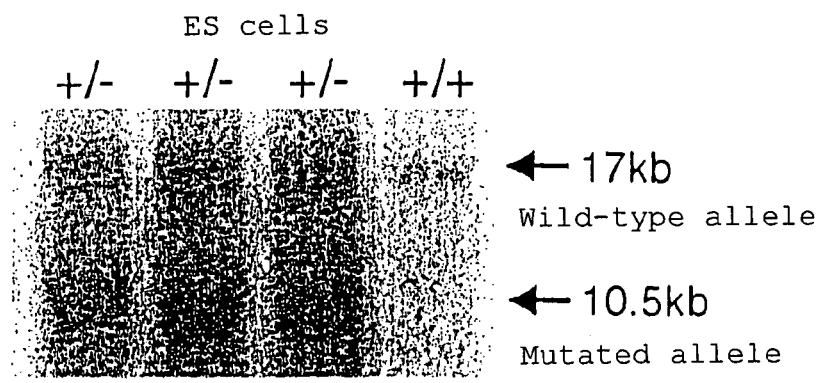
FIG. 2 shows the results of Southern blotting of ES-cell-derived DNA samples which have been digested with SpeI and EoRV. The bands of 17 kb are obtained from wild-type alleles, and those of 10.5 kb are from mutated alleles.
Figure 3:
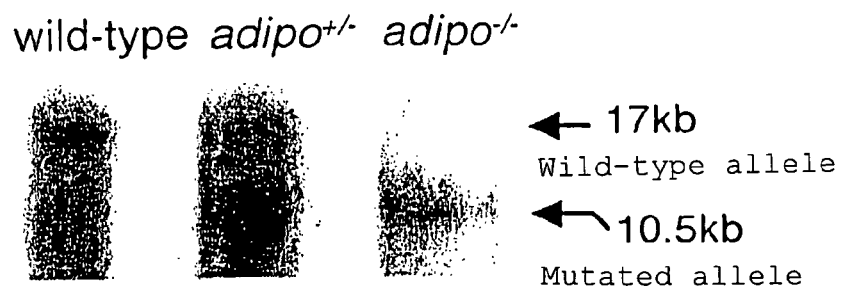
FIG. 3 shows the results of Southern blotting of SpeI- and EoRV-digested DNA samples from a wild-type mouse, a hetero-deficient (adipo +/−) mouse, and a homo-deficient (adipo −/−) mouse. The bands of 17 kb are obtained from wild-type alleles, and those of 10.5 kb are from mutated alleles.

1. With an aim to knock out the mouse adiponectin gene, a targeting vector in which exons 2 and 3 that encode adiponectin were replaced with a neo resistant gene was prepared. Separate 5 homologous recombinant clones were confirmed through Southern blotting (FIG. 2). From ES cells having 129/Sv as a background, chimeric mice were produced, and in order to create a hetero-deficient mouse, they were crossbred with BI/6. The genotype was confirmed through Southern blotting (FIG. 3).

(2) Insulin Tolerance Test

Human insulin was intraperitoneally administered to test mice in an amount of 0.7 mU per gram (body weight), and the mice were fasted during the tolerance test. The blood was collected from the tail vein, and blood sugar level was measured by means of a Glutest Ace (registered trademark, product of Sanwa Kagaku Kenkyusho Co., Ltd.).

(3) Glucose Tolerance Test

Glucose was perorally administered to test mice in an amount of 1.5 mg per gram (body weight). Prior to the administration, the mice had been fasted for at least 16 hours. The blood was collected from the fundus vein, and blood sugar level and insulin level were measured by means of a Glutest Ace (registered trademark, product of Sanwa Kagaku Kenkyusho Co., Ltd.) and a rat insulin RIA kit (product of Amersham Pharmacia Biotech), respectively.

(4) Measurement of Blood Lipid Level

After the test mice were fasted for 16 hours, levels of free fatty acid, neutral fat, and total cholesterol, all in blood, were measured by means of a NEFAC-test, a TGL-type, and a Tchol E-type (product of Wako), respectively.

(5) Measurement of Blood Leptin Level and Blood Adiponectin Level

After the mice were fasted for 16 hours, levels of leptin and adiponectin, both in blood, were measured by means of a Quintikine M kit (product of R&D) and an adiponectin RIA kit (product of Linco), respectively.

(6) Creation of a Thick Vascular Intima Model Through Cuff Placement

A 2.0-mm polyethylene tube (PE-50) was placed in the femoral artery. When two weeks had passed, the artery was press-fixed with formalin, and removed together with the opposite-side, uncuffed artery, which served as a control artery. Each of the thus-removed blood vessels was sliced to obtain continuous ring-shaped specimens, each having a length of 10 mm. Ten specimens were taken and HE staining was performed. The inner diameter of the blood vessel, the thickness of the intima, and the thickness of the media were measured, and intima/media ratio was calculated.

(7) Preparation of gAd-Overexpressed Mice

According to the method described in Diabetes 48, 1822-1829 (1999), a fused gene containing a human SAP promoter and mouse gAd cDNA was prepared. Purified Hind III-XhoI fragments were microinjected to pronuclei of fertilized ova of C57BL6 mice (product of Clea Japan, Inc.). Tail DNA samples obtained from the resultant transgenic mice were subjected to Southern blotting through use of a gAd cDNA probe for the Bgl II/Hinc II site of gAd, whereby gAd over-expression of the transgenic mice was confirmed.

(8) Production of gAd-Overexpressing apoE-Deficient Mice gAd-overexpressing apoE-deficient mice were crossbred, to thereby produce gAd-overexpressing apoE-hetero-deficient mice. The resultant mice were crossed further with apoE-deficient mice, to thereby create apoE-deficient mice exhibiting over-expression of gAd.

(9) Measurement of Blood Sugar Level and Lipid Level

Mice were fed until they were full, and their blood sugar level and levels, in blood, of free fatty acid, neutral fat, and total cholesterol were measured by means of a Glutest Ace (registered trademark, product of Sanwa Kagaku Kenkyusyo Co., Ltd.), an NEFA C-test, a TGL-type, and a Tchol E-type (Products of Wako), respectively.

(10) Evaluation of the Size of Arteriosclerotic Foci

From each of gAd-overexpressed apoE-deficient mice (4 months old) and control apoE-deficient mice, the aortic arch and the descending aorta were removed, fixed with formalin, and then subjected to staining with Sudan IV. The arteriosclerotic foci were evaluated in terms of their size.

(11) Evaluation in Terms of Buildup of Cholesterol Ester, Expression Level of Scavenger Receptor A, and Macrophage Accumulation Frozen samples of continuous ring-shaped specimens of the annulus portion of the aorta were prepared. Ten such samples were subjected to immunostaining by use of Oil Red O, anti-scavenger receptor A antibody, or anti-Mac3 antibody (a macrophage-specific marker), whereby buildup of cholesterol ester, expression level of scavenger receptor A, and macrophage accumulation were evaluated, respectively.

B. Results (1) Mouse-Adiponectin-Gene-Deficient Mice

Figure 4:
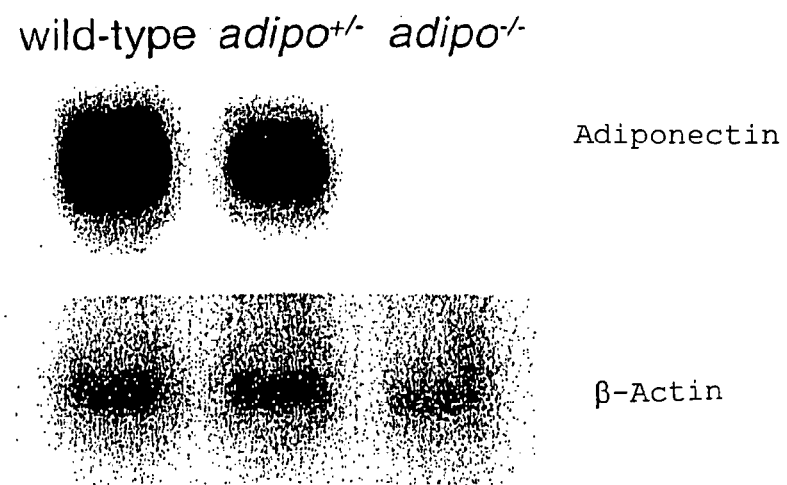
FIG. 4 shows the results of Northern blotting of white adipose tissue samples from a wild-type mouse, a hetero-deficient (adipo +/−) mouse, and a homo-deficient (adipo −/−) mouse.
Figure 5:
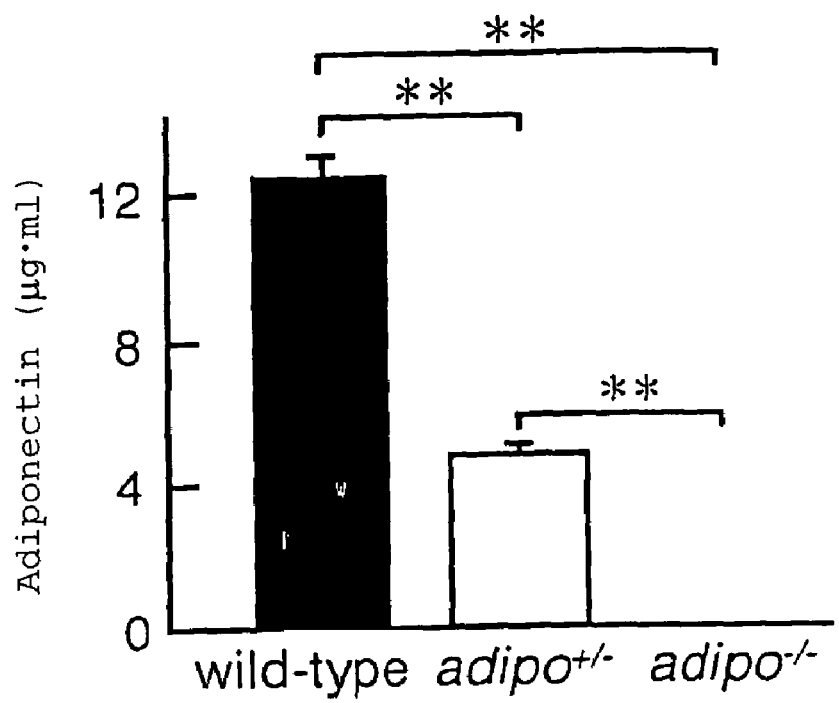
FIG. 5 shows blood adiponectin level of a wild-type mouse, a hetero-deficient (adipo +/−) mouse, and a homo-deficient (adipo −/−) mouse. **$P<0.01$.
Figure 6:
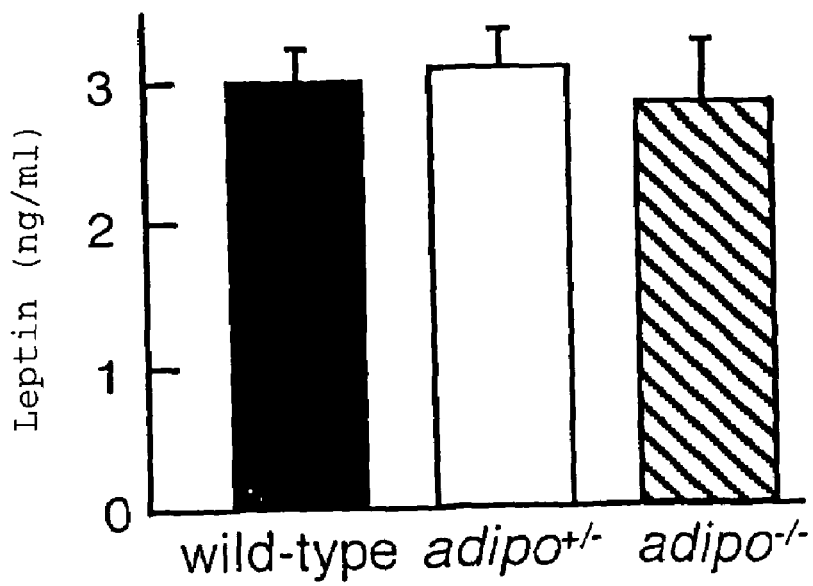
FIG. 6 shows blood leptin level of a wild-type mouse, a hetero-deficient (adipo +/−) mouse, and a homo-deficient (adipo −/−) mouse.

Through Northern blotting of white adipose tissue, the expression level of adiponectin in the hetero-deficient mice was found to be reduced by about 60%, and the homo-deficient mice were found to exhibit completely no adiponectin expression (FIG. 4). Indeed, when blood adiponectin level was measured in the hetero-deficient mice, the magnitude of reduction was found to be about 60%, and the level in the hetero-deficient mice was found to be lower than the undetectable level (FIG. 5). With respect to the blood leptin level, no difference was observed (FIG. 6).

(2) Insulin Resistance of Mouse-Adiponectin-Gene-Deficient Mice

Figure 7:
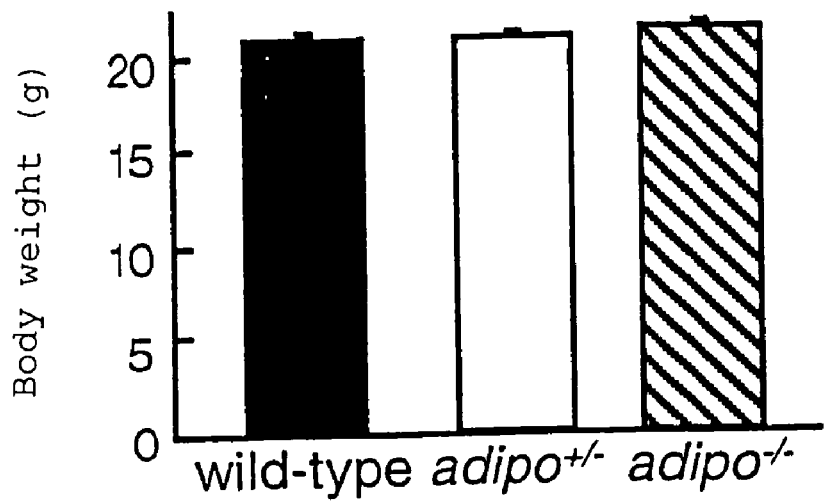
FIG. 7 shows the body weight, at 6 weeks of age, of a wild-type mouse, a hetero-deficient (adipo +/−) mouse, and a homo-deficient (adipo −/−) mouse.
Figure 8:
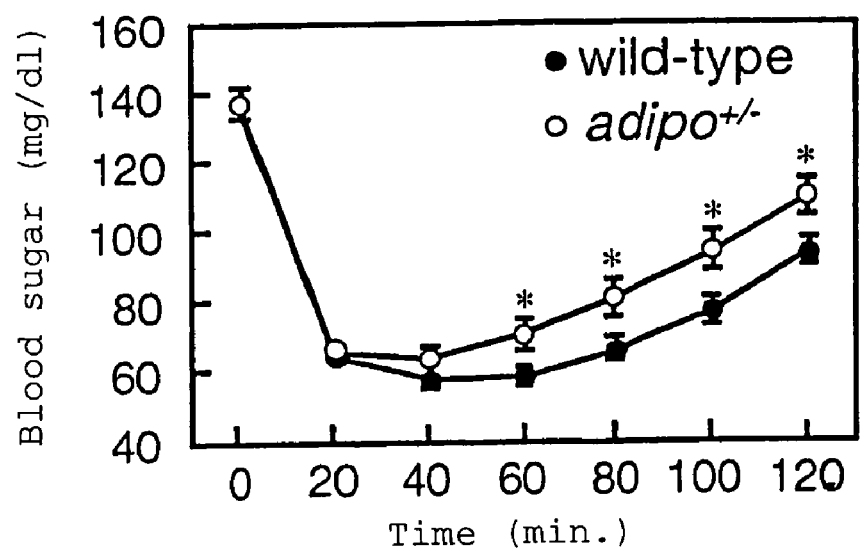
FIG. 8 shows the results of an insulin tolerance test performed on a wild-type mouse and a hetero-deficient (adipo +/−) mouse at 6 weeks of age. *$P<0.05$.

In three groups of 6-week-old mice; i.e., wild-type group, hetero-deficient (adipo +/−) group, and homo-deficient (adipo −/−) group, there was no difference in terms of body weight (FIG. 7). The 6-week-old wild-type mice and hetero-defective mice of the same age were subjected to an insulin tolerance test, to thereby check their insulin sensitivity. The degree of reduction in blood sugar level in response to exogenous insulin was statistically significantly low in the hetero-deficient mice, proving that the hetero-deficient mice had insulin resistance (FIG. 8).

Figure 9:
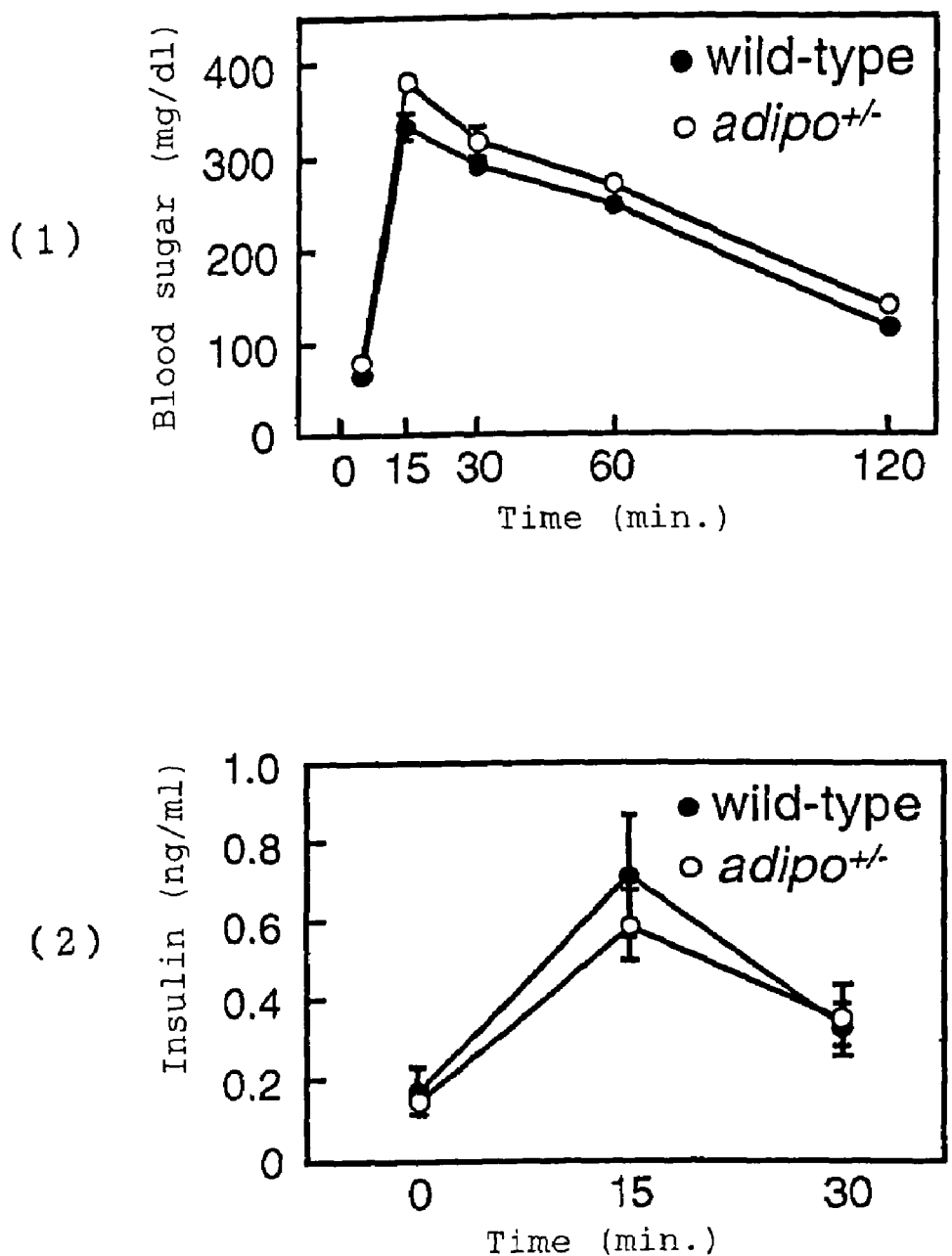
FIG. 9 shows the results of a glucose tolerance test performed on a wild-type mouse and a hetero-deficient (adipo +/−) mouse at 6 weeks of age. *$P<0.05$.
Figure 10:
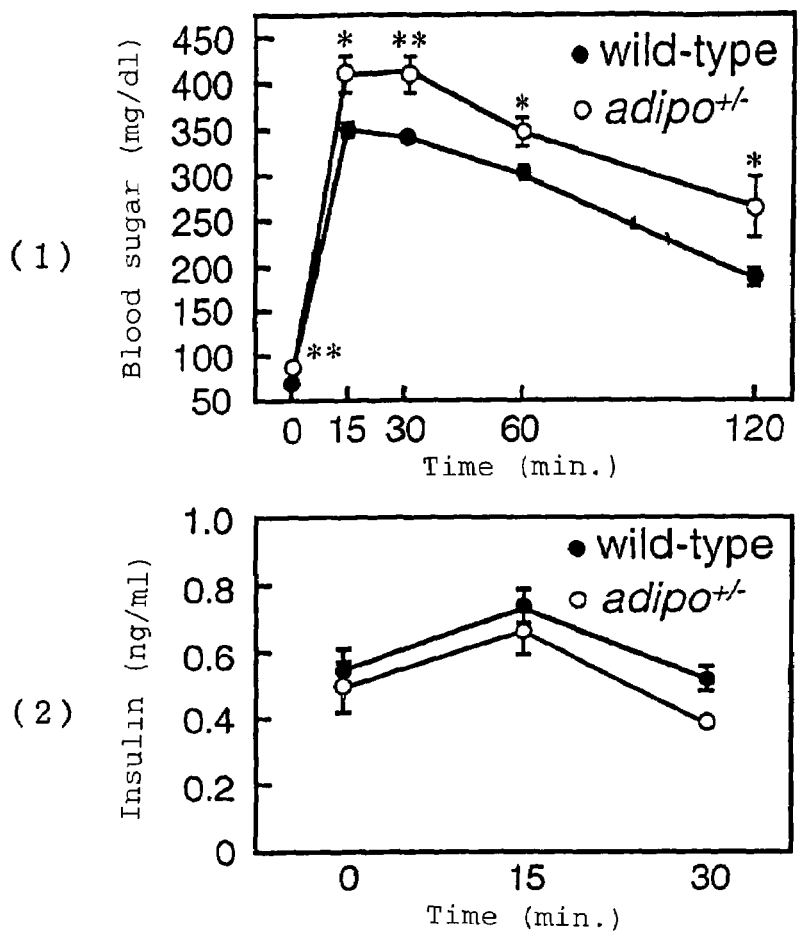
FIG. 10 shows the results of a glucose tolerance test performed on a wild-type mouse and a hetero-deficient (adipo +/−) mouse after having loaded with a high-fat diet for 10 weeks. *$P<0.05$, **$P<0.01$.

Next, a glucose tolerance test was performed. No difference was observed between the two groups of wild-type mice and hetero-deficient mice in terms of blood sugar or insulin level (FIG. 9). However, as compared with the wild-type mice, the hetero-deficient mice, after having been loaded with 10-week high fat diet, exhibited a significantly high blood sugar level before and after loading with glucose, though the body weight remained in a similar level (FIG. 10).

Afterwards, analysis on the homo-deficient mice was performed.

Figure 11:
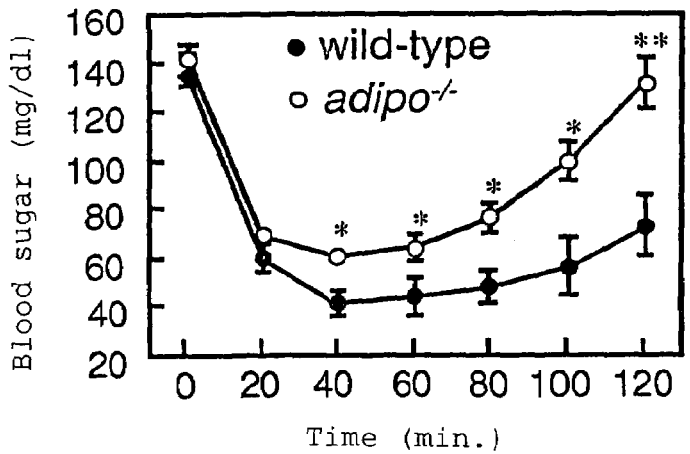
FIG. 11 shows the results of an insulin tolerance test performed on a wild-type mouse and a homo-deficient (adipo −/−) mouse, at 6 weeks of age. *$P<0.05$, **$P<0.01$.

An insulin tolerance test performed on 6-week-old wild-type mice and homo-deficient mice of the same age. As compared with the wild-type mice or the hetero-deficient mice, the degree of reduction in blood sugar level in response to exogenous insulin was statistically significantly low in the homo-deficient mice, proving that the homo-deficient mice had insulin resistance higher than the corresponding levels of the wild-type mice and homo-deficient mice (FIG. 11).

Figure 12:
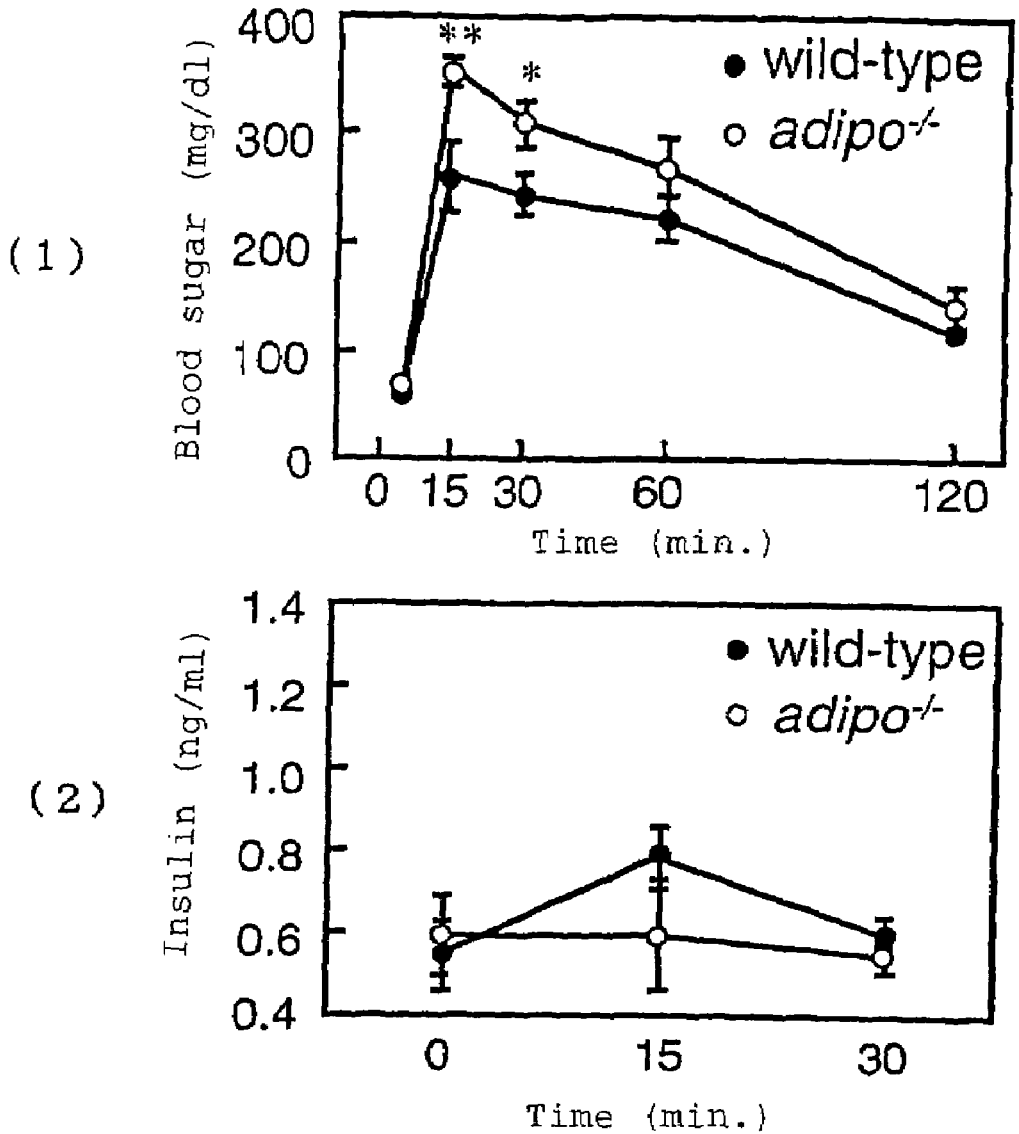
FIG. 12 shows the results of a glucose tolerance test performed on a wild-type mouse and a hetero-deficient (adipo +/−) mouse, at 6 weeks of age. *$P<0.05$, **$P<0.01$.

Next, a glucose tolerance test was performed. In both stages of during fasting and after glucose loading, the homo-deficient mice exhibited blood sugar levels higher than the case of wild-type mice. This substantiates that homo-deficient mice had slightly impaired glucose tolerance in addition to insulin resistance (FIG. 12). Before administration and 30 minutes after administration, no difference was observed between the wild-type group and the homo-deficient group in terms of the insulin levels before and after glucose loading. However, the homo-deficient mice showed a somewhat low insulin level at 15 min (FIG. 12).

(3) Blood Neutral Fat Level in Adiponectin Homo-Deficient Mice

Figure 13:
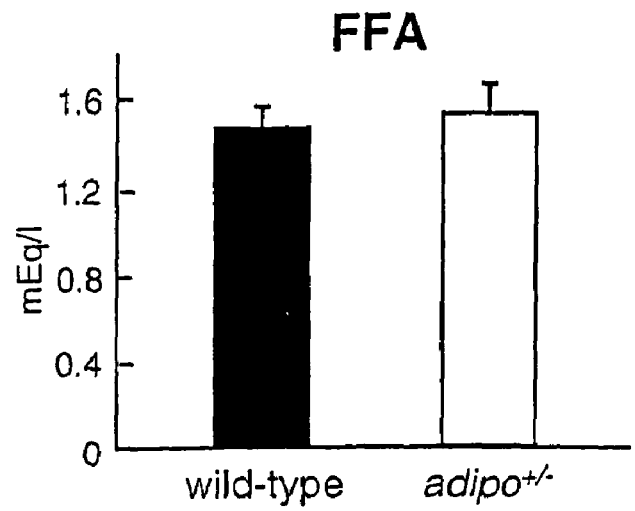
FIG. 13 shows levels, in blood, of free fatty acid (FFA), neutral fat (TG), total cholesterol (TC) of a wild-type mouse and a hetero-deficient (adipo +/−) mouse.
Figure 13:
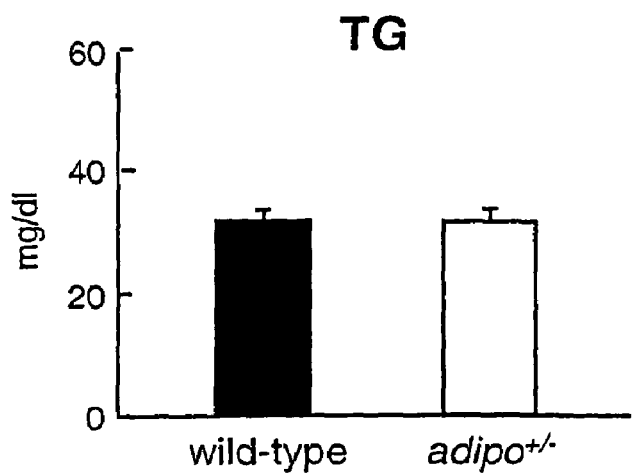
Figure 13:
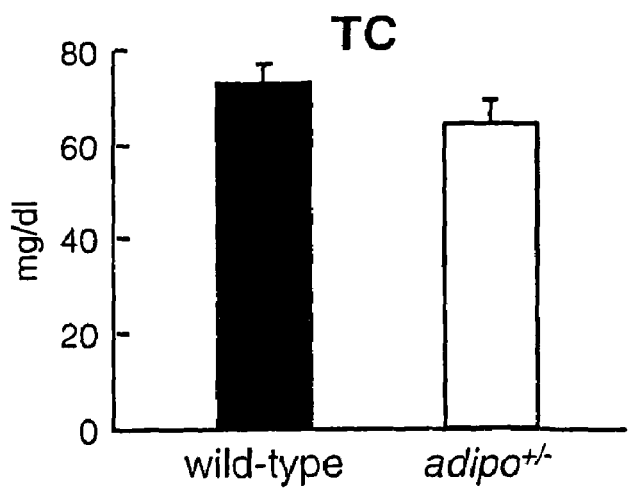
Figure 14:
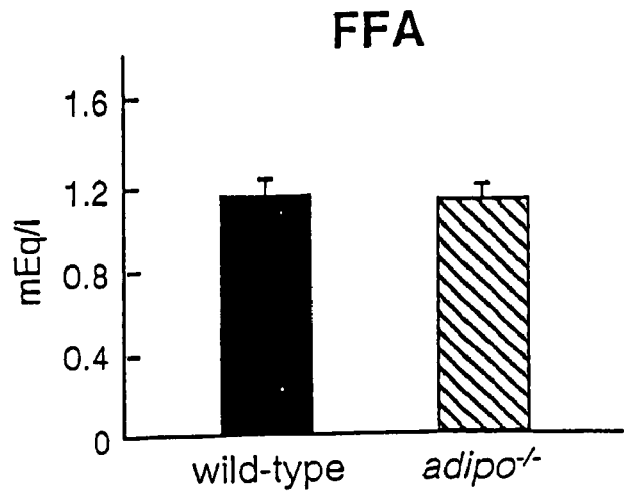
FIG. 14 shows levels, in blood, of free fatty acid (FFA), neutral fat (TG), total cholesterol (TC) of a wild-type mouse and a homo-deficient (adipo −/−) mouse.
Figure 14:
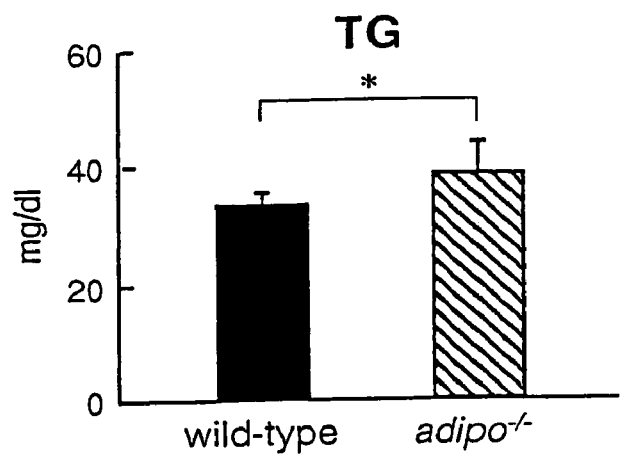
Figure 14:
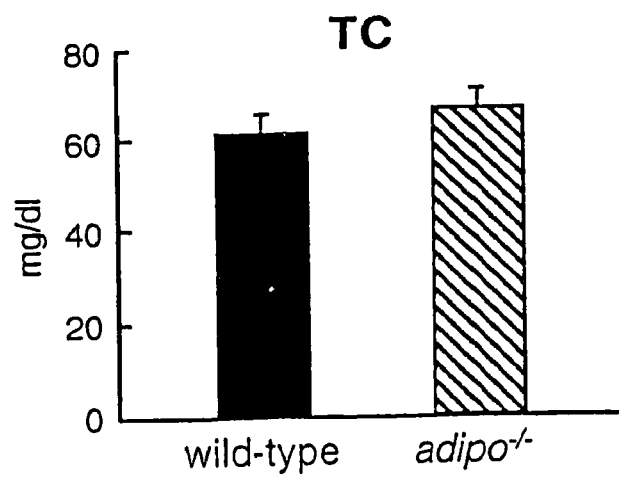

In order to check the effect of adiponectin on lipid metabolism, levels, in blood, of free fatty acid (FFA), neutral fat (TG), and total cholesterol (TC) were determined in wild-type, hetero-deficient, and homo-deficient mice (FIGS. 13 and 14). The hetero-deficient mice did not show any difference in level of any of the three test items as compared with the wild-type mice (FIG. 13). However, the homo-deficient mice showed significantly higher blood neutral fat levels than the wild-type mice (FIG. 14).

Figure 15:
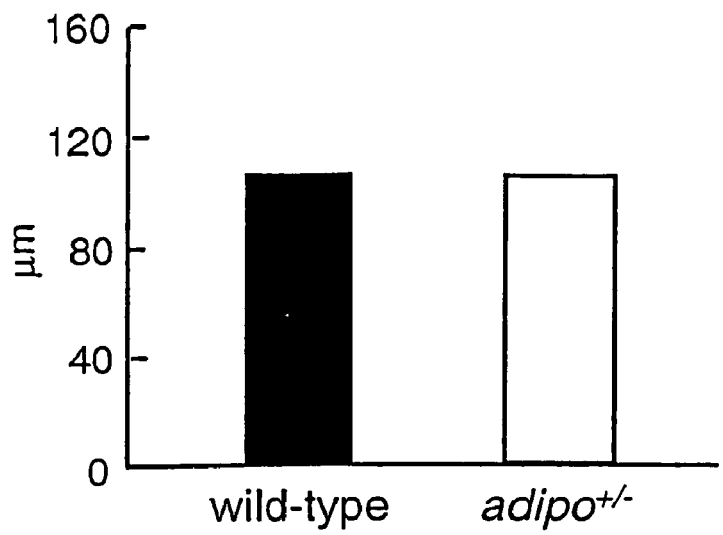
FIG. 15 shows the inner diameter of a blood vessel of a wild-type mouse and a hetero-deficient (adipo +/−) mouse, as measured two weeks after the mice underwent cuff placement.
Figure 16:
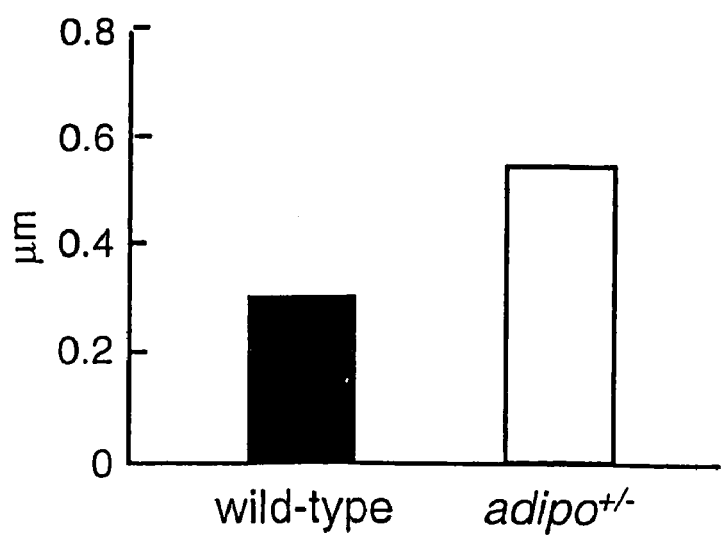
FIG. 16 shows the degree of intimal thickening of a wild-type mouse and a hetero-deficient (adipo +/−) mouse, as measured two weeks after the mice underwent cuff placement.
Figure 17:
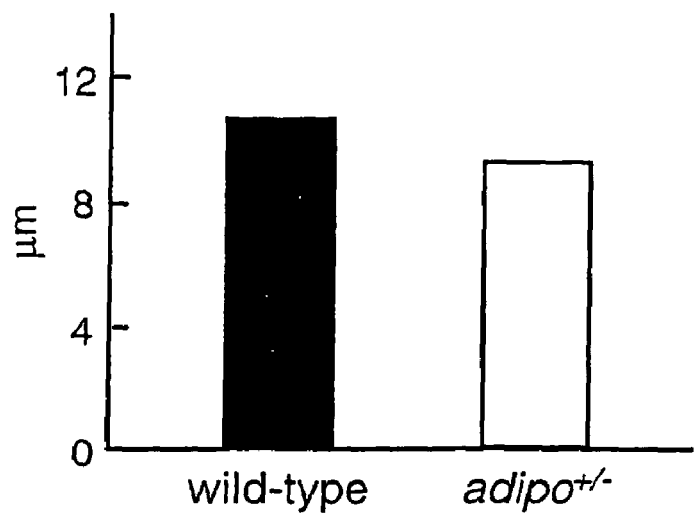
FIG. 17 shows the degree of medial thickening of a wild-type mouse and a hetero-deficient (adipo +/−) mouse, as measured two weeks after the mice underwent cuff placement.
Figure 18:
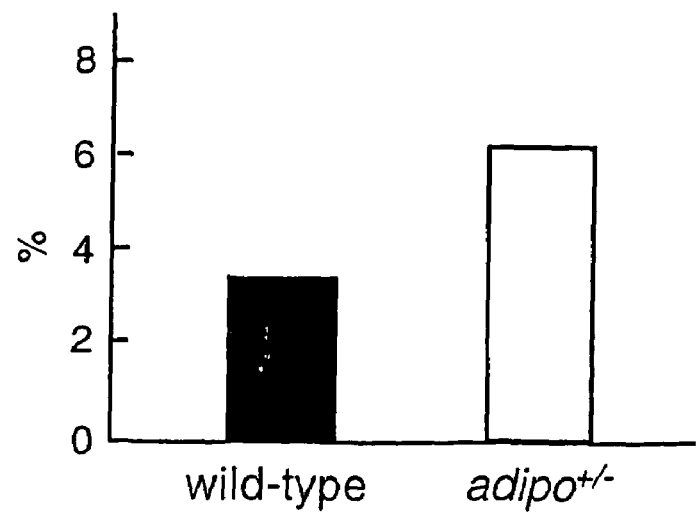
FIG. 18 shows the intima/media ratio of a wild-type mouse and a hetero-deficient (adipo +/−) mouse, as measured two weeks after the mice underwent cuff placement.

(4) Thickening of Intima in Cuff-Injured Models of Mouse Adiponectin Hetero-Deficient Mice In order to investigate the effect of adiponectin on arteriosclerosis, the degree of intimal thickening induced by cuff placement was measured in the wild-type mice and the hetero-deficient mice for comparison therebetween. No difference was observed between the two groups in terms of the vascular inner diameter after cuff-induced injury was created (FIG. 15). When 2 weeks had elapsed after creation of cuff injury, the hetero-deficient mice showed about 1.8 times the thickness of the intima of the wild-type mice (FIG. 16). However, no difference was observed between the two groups in terms of the thickness of the media (FIG. 17). The intima/media ratio of the hetero-deficient group exhibited a ratio about two-fold that of the wild-type mice (FIG. 18).

Figure 19:
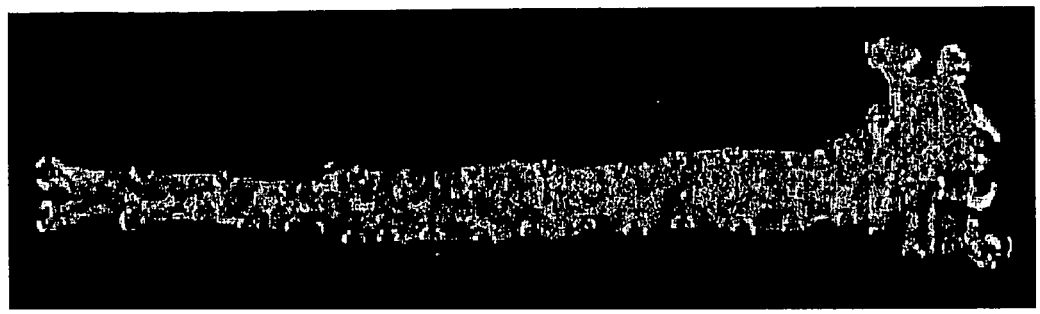
FIG. 19 shows the foci of arteriosclerosis in an apoE-deficient (apoE−/−:a) mouse and a gAd-overexpressed apoE-deficient (gAd Tg apoE−/−:b) mouse.
Figure 19:
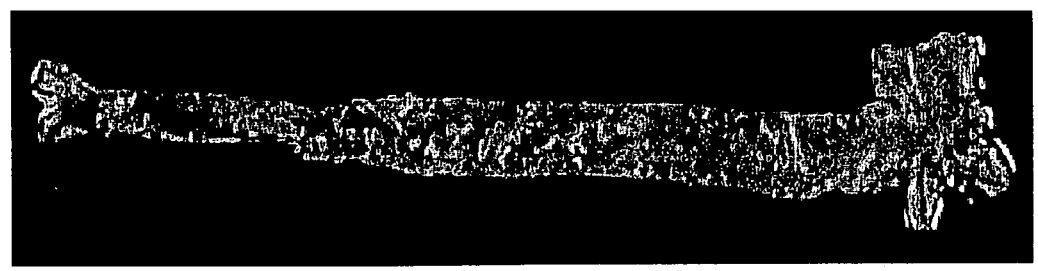
Figure 20:
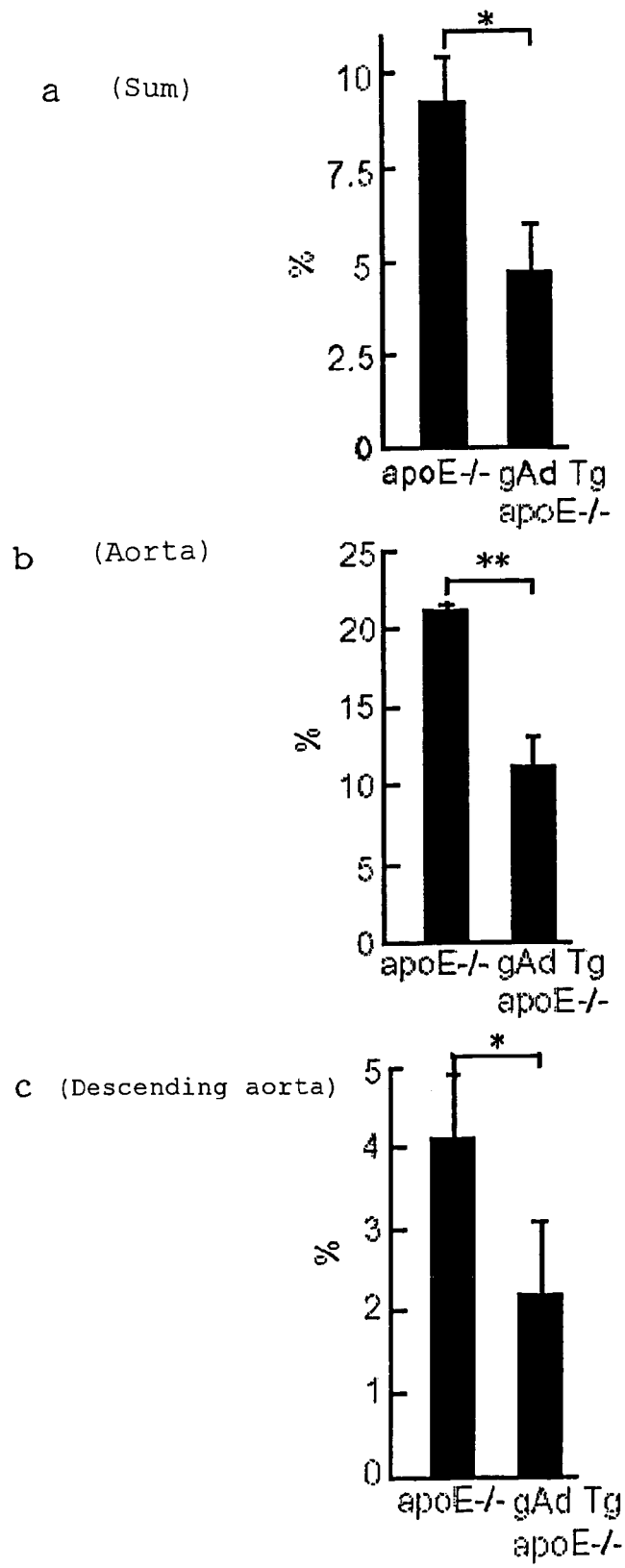
FIG. 20 shows the areas of the foci of arteriosclerosis in an apoE-deficient (apoE−/−) mouse and a gAd-overexpressed apoE-deficient (gAd Tg apoE−/−) mouse (aortic arch (b), descending aorta (c), and their sum (a)).

(5) Prevention of the Onset of Arteriosclerosis in gAd-Over-expressing apoE-Deficient Mice ApoE-deficient mice, which represent a spontaneous arteriosclerosis model, were caused to overexpress gAd and studied whether or not onset of arteriosclerosis was prevented. The results are shown in FIGS. 19 and 20. In FIG. 19, "a" shows the results of Sudan IV staining of aorta samples from apoE-deficient mice, and "b" shows the results of Sudan IV staining of aorta samples from gAd-overexpressed apoE-deficient mice. As is evident from the comparison between "a" and "b," gAd-overexpressed apoE-deficient mice clearly show a reduction in the incidence of arteriosclerotic foci. FIG. 20 shows comparison with respect to the area of arteriosclerotic foci. FIG. 20 shows that over-expression of gAd caused significant reduction in the area of arteriosclerotic foci, which are stained with Sudan IV, in any case of aortic arch (b), descending aorta (c), the sum of the mentioned two cases (a), indicating arresting of the onset of arteriosclerosis.

(6) Effect of gAd Overexpression on Arteriosclerosis Risk Factors in apoE-Deficient Mice on a Normal Diet The body weight, blood sugar level, and levels, in blood, of free fatty acid, neutral fat, and total cholesterol of gAd-overexpressed apoE-deficient mice on a normal diet are shown in Table 1.

TABLE 1

| | Mouse | | |
|---|---|---|---|
| | apoE−/− | gAd Tg apoE−/− | Statistical significance |
| Body weight (g) | 29.8 ± 1.2 | 29.9 ± 1.5 | none |
| Plasma glucose level (mg/dl) | 145 ± 4 | 152 ± 8 | none |
| Serum total cholesterol level (mg/dl) | 541 ± 49 | 509 ± 32 | none |
| Serum triglyceride level (mg/dl) | 127 ± 52 | 104 ± 24 | none |
| Serum free fatty acid level (mEq/L) | 0.53 ± 0.08 | 0.57 ± 0.04 | none |

Mean ± s.e. (n = 5)

As shown in Table 1, when apoE-deficient mice on a normal diet were caused to over-express gAd, no significant effect was exerted on arteriosclerosis risk factors such as body weight and blood sugar, and free fatty acid, neutral fat, and total cholesterol in blood. This suggests that gAd possibly acts on vascular walls or macrophages directly, to thereby exhibit anti-arteriosclerotic activity.

(7) Mechanism of Arresting Onset of Arteriosclerosis by gAd

Figure 21:
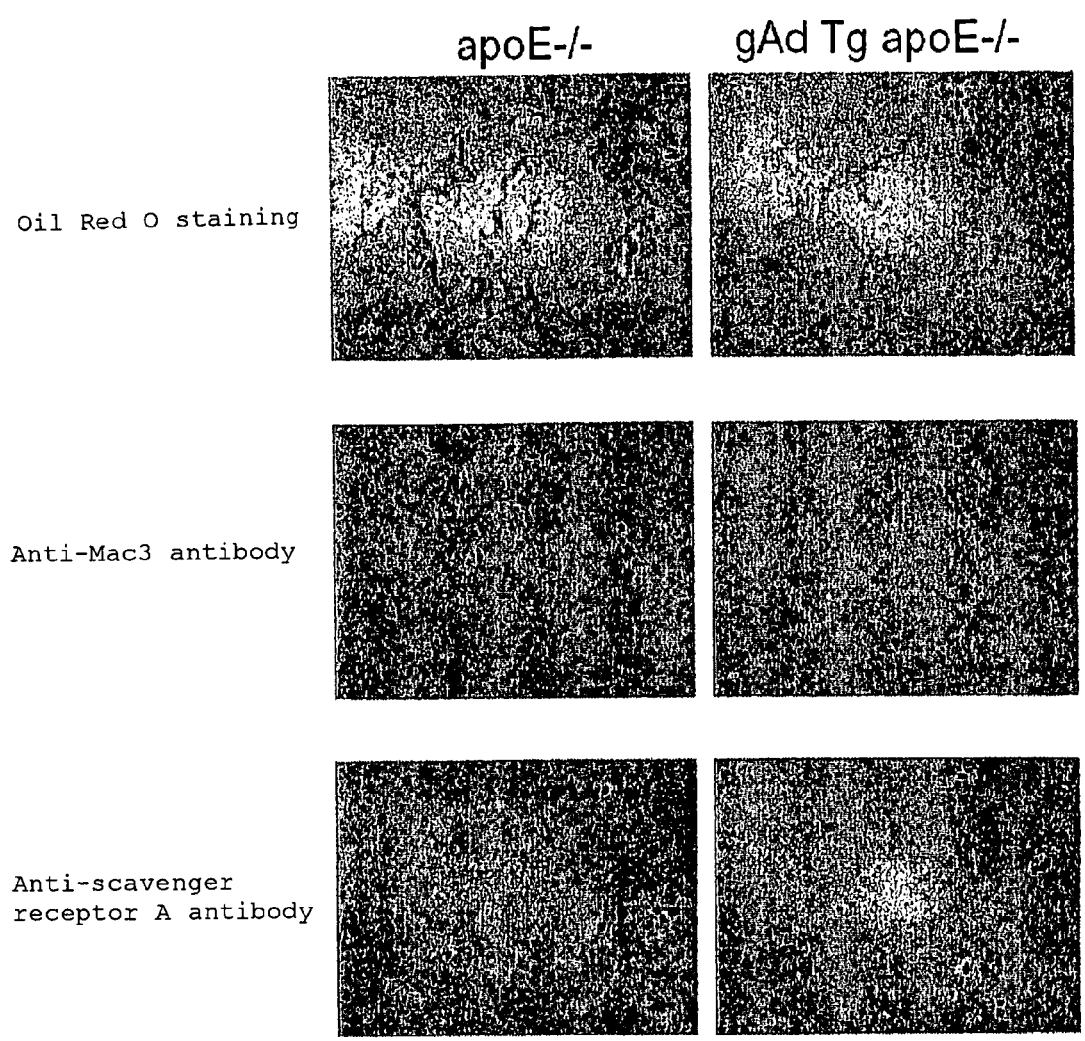
FIG. 21 shows the results of Oil Red O staining, reaction with anti-Mac3 antibody, and reaction with anti-scavenger receptor A antibody as observed in an apoE-deficient (apoE−/−) mouse and a gAd-overexpressed apoE-deficient (gAd Tg apoE−/−) mouse.

With an aim to elucidate the mechanism of the interaction between gAd and vascular walls or macrophages, frozen samples of continuous ring-shaped slices of annulus portion of the aorta were subjected to immunostaining by use of Oil Red O, anti-scavenger receptor A antibody, and a macrophage-specific marker; i.e., anti-Mac3 antibody. As a result, as shown in FIG. 21, over-expression of gAd, though having no significant impact on accumulation of macrophages, were found to reduce the expression level of scavenger receptor A, suppress buildup of lipids in macrophages, and arrest the onset of arteriosclerosis.

INDUSTRIAL APPLICABILITY

The present invention provides a preventive or therapeutic agent capable of directly preventing intimal thickening, which constitutes an essential feature of arteriosclerosis, wherein this effect can be attained through arresting the onset and development of arteriosclerosis by reducing the expression level of scavenger receptor A in arterial walls and preventing lipid buildup in macrophages.

The invention claimed is:

1. A method for treating arteriosclerosis, comprising administering a C-terminal globular domain of adiponectin, in an effective amount to a subject in need thereof to treat arteriosclerosis, wherein the C-terminal globular domain consists of amino acids 114 to 239 of SEQ ID NO:2 or amino acids 111 to 242 of SEQ ID NO:2.

2. The method as claimed in claim 1, wherein arteriosclerosis is from intimal thickening.

3. A method for down-regulating expression of scavenger receptor A in a subject, comprising administering a C-terminal globular domain of adiponectin, in an effective amount to the subject to down-regulate expression of scavenger receptor A, wherein the C-terminal globular domain consists of amino acids 114 to 239 of SEQ ID NO:2 or amino acids 111 to 242 of SEQ ID NO:2.

* * * * *